(12) United States Patent　　(10) Patent No.: US 9,138,243 B2
Gustilo et al.　　(45) Date of Patent: Sep. 22, 2015

(54) BONE COMPACTOR

(75) Inventors: Ramon B. Gustilo, Eden Prairie, MN (US); Jude L. Sasing, Quezon (PH); Joan E. Bechtold, Minneapolis, MN (US); Andrew L. Freeman, Falcon Heights, MN (US); William James Camisa, San Francisco, CA (US)

(73) Assignee: Orthopaedic International, Inc. (PH)

( * ) Notice: Subject to any disclaimer, the term of this patent is extended or adjusted under 35 U.S.C. 154(b) by 580 days.

(21) Appl. No.: 13/422,567

(22) Filed: Mar. 16, 2012

(65) Prior Publication Data

US 2012/0245646 A1　Sep. 27, 2012

Related U.S. Application Data

(60) Provisional application No. 61/467,660, filed on Mar. 25, 2011.

(51) Int. Cl.
*A61B 17/56* (2006.01)
*A61B 17/16* (2006.01)
*A61B 17/88* (2006.01)

(52) U.S. Cl.
CPC .......... *A61B 17/164* (2013.01); *A61B 17/8858* (2013.01); *A61B 17/8855* (2013.01)

(58) Field of Classification Search
CPC ............. A61B 17/8858; A61B 17/164; A61B 17/8852; A61B 17/8855
USPC ................... 606/86 R, 313; 623/23.15–23.38
See application file for complete search history.

(56) References Cited

U.S. PATENT DOCUMENTS

| | | | | |
|---|---|---|---|---|
| 3,846,846 | A | * | 11/1974 | Fischer ...................... 623/23.18 |
| 4,462,394 | A | * | 7/1984 | Jacobs ............................. 606/94 |
| 4,520,511 | A | * | 6/1985 | Gianezio et al. ........... 623/22.46 |
| 4,695,283 | A | * | 9/1987 | Aldinger .................... 623/23.24 |
| 5,480,400 | A | | 1/1996 | Berger |
| 5,788,703 | A | | 8/1998 | Mittelmeier et al. |
| 5,800,437 | A | | 9/1998 | Gustilo et al. |
| 5,876,459 | A | * | 3/1999 | Powell ....................... 623/23.15 |
| 6,126,659 | A | | 10/2000 | Wack |
| 6,228,123 | B1 | * | 5/2001 | Dezzani ..................... 623/23.32 |
| 6,355,069 | B1 | * | 3/2002 | DeCarlo et al. ........... 623/23.26 |
| 7,261,720 | B2 | | 8/2007 | Stevens et al. |
| 7,935,117 | B2 | * | 5/2011 | Sackett et al. .................. 606/80 |
| 2001/0011174 | A1 | | 8/2001 | Reiley et al. |
| 2002/0026197 | A1 | * | 2/2002 | Foley et al. .................... 606/105 |
| 2005/0070898 | A1 | * | 3/2005 | Jones .............................. 606/53 |
| 2005/0124989 | A1 | * | 6/2005 | Suddaby ......................... 606/53 |
| 2007/0010845 | A1 | * | 1/2007 | Gong et al. ................... 606/192 |
| 2007/0276392 | A1 | | 11/2007 | Beyar et al. |
| 2008/0275449 | A1 | * | 11/2008 | Sackett et al. .................. 606/80 |
| 2009/0177206 | A1 | * | 7/2009 | Lozier et al. ................... 606/93 |
| 2010/0241178 | A1 | | 9/2010 | Tilson et al. |
| 2011/0077747 | A1 | * | 3/2011 | Geller ....................... 623/23.15 |

* cited by examiner

*Primary Examiner* — Zade Coley
(74) *Attorney, Agent, or Firm* — Kagan Binder, PLLC (57) ABSTRACT

A bone compacting device for compacting cancellous bone within a bone cavity, the bone compacting device including a body having a plurality of segments, wherein each segment is adjacent to at least one adjacent segment between a first end and a second end of the body, and wherein each of the plurality of segments is independently expandable to contact the cancellous bone.

10 Claims, 8 Drawing Sheets

BONE COMPACTOR

CROSS-REFERENCE TO RELATED APPLICATION

This application claims the benefit under 35 U.S.C. §119 (e) of U.S. Provisional Patent Application No. 61/467,660, filed Mar. 25, 2011 and titled "Bone Compactor", which is incorporated herein by reference in its entirety.

TECHNICAL FIELD

The present invention relates to the preparation of a bone for the implantation of a prosthesis. In particular, the devices of the invention are used in the preparation of a proximal cavity of a human femur so that it can receive a hip stem implant of a total or partial hip replacement system, although the devices can be applicable for use in other areas where bone compaction is desirable.

BACKGROUND

Hip stems are available in different sizes such as small, medium, and the like, in order to accommodate the needs of individual patients and their unique anatomies. In many cases, different shaped hip stems are also available, such as primary stems or revisions stems. During surgery, it is desirable for the surgeon to carve out a portion of the inner cavity of the femur to closely match size and shape of an available hip stem, since different individual patients have bones with different anatomical shapes. One common practice is to shape the proximal cavity of the femur by removing part of the inner cancellous bone using a sharp broach or rasp. However, laboratory studies have shown that if cancellous bone is compacted instead of being removed from the bone cavity, it can provide a more stable bed for the implant. That is, compacting the bone can provide for a stronger interface connection between an implant and the bone, which can be true for both cemented and cementless implant applications.

Certain devices are known in the art for compacting cancellous bone, such as a bone tamp of the type described in U.S. Pat. No. 5,800,437 (Gustilo et al.), which patent is incorporated herein by reference in its entirety. However, such bone tamps have certain limitations due to the forces exerted on the femur when the bone tamp is pounded into the bone. Thus, there is a need to provide alternative devices and methods for compacting cancellous bone in a controlled manner, without exerting undue force on the bone.

SUMMARY

A bone compacting device of the invention is provided for compacting cancellous bone within a bone cavity, such as can be done to prepare a cavity of a femur prior to receiving a hip stem implant, for example. In one aspect of the invention, a bone compacting device includes an elongated member and a port at a proximal end of the elongated member, wherein the port is in communication with a supply of an inflation medium so the elongated member is expandable in response to a quantity of the inflation medium entering the elongated member through the port. In another aspect of the invention, a bone compacting device includes a body comprising a plurality of segments, wherein each segment is adjacent to at least one adjacent segment between a first end and a second end of the body and along a length of the body, wherein each of the plurality of segments is independently expandable to contact the cancellous bone. The plurality of segments can include ring segments and the device can further include a core member having an outer surface over which the plurality of segments are adjacently positioned.

BRIEF DESCRIPTION OF THE DRAWINGS

The present invention will be further explained with reference to the appended Figures, wherein like structure is referred to by like numerals throughout the several views, and wherein.

DETAILED DESCRIPTION

Figure 1:
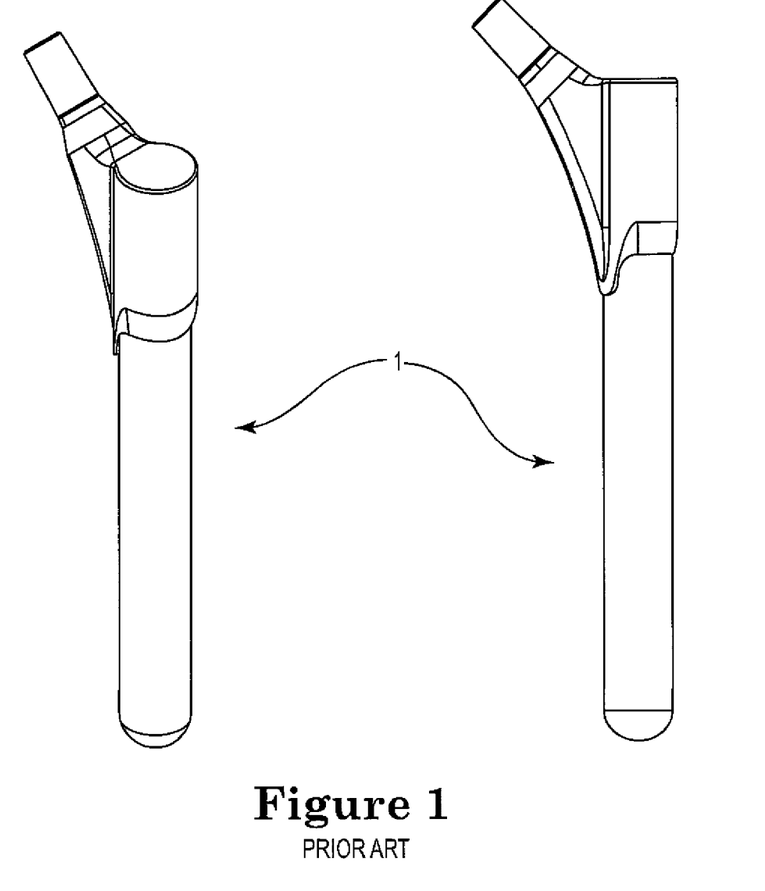
FIG. 1 includes a perspective view and a front view of a prior art hip stem prosthesis.

Referring now to the Figures, wherein the components are labeled with like numerals throughout the several Figures, and initially to FIG. 1, a hip stem prosthesis 1 of the type generally known in the art is illustrated. Such a hip stem prosthesis can include an elongated portion that is positionable in the intramedullary canal of the femur of a patient, for example, along with a shoulder or collar at its proximal end.

Figure 2:
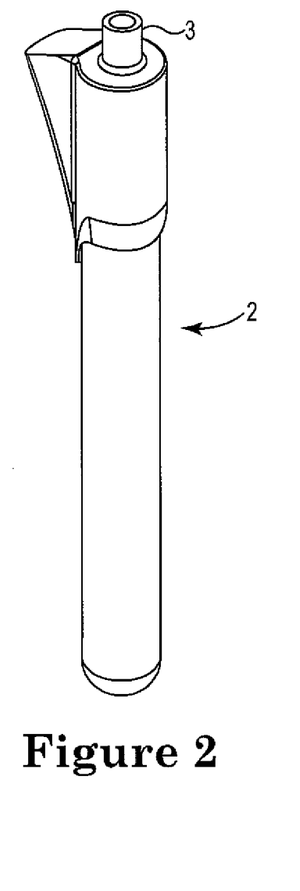
FIG. 2 is a perspective view of an embodiment of a bone compactor of the invention.

One exemplary embodiment of a bone compactor 2 of the invention is illustrated in FIG. 2. The compactor 2 includes an inflatable or expandable structure that is made of a flexible material (such as rubber, plastic, impermeable fabric, or combinations thereof, for example). The compactor 2 includes an elongated portion with a pressure connector or port 3 at its proximal end. Prior to positioning the compactor 2 within a bone of a patient, it can be in a deflated or semi-inflated condition so that it will fit relatively easily into the femur. The compactor 2 is then placed inside the femur and inflated or expanded using a gas or liquid medium, such as by introduction of such materials through the pressure connector 3. The pressure at which the gas or liquid is delivered to the compactor 2 can be set or monitored and controlled so that it is sufficient to compress the cancellous bone by a desired amount, but so that it is not so high that it causes the bone to fracture. When the compactor 2 is inflated by a desired amount, it generally assumes the shape and size of the hip stem prosthesis that will be positioned within that area of the bone. For example, the compactor 2 can be inflated by a desired amount to compact the cancellous bone and create a cavity that matches the size and shape of a hip stem prosthesis that will be implanted in that bone.

Figure 3:
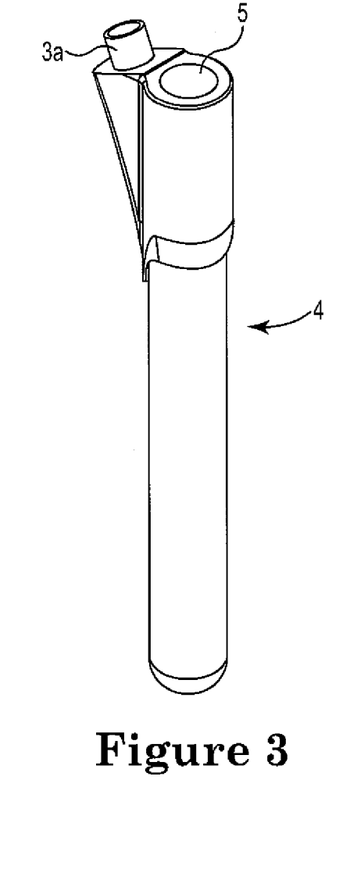
FIG. 3 is a perspective view of another embodiment of a bone compactor of the invention.
Figure 4:
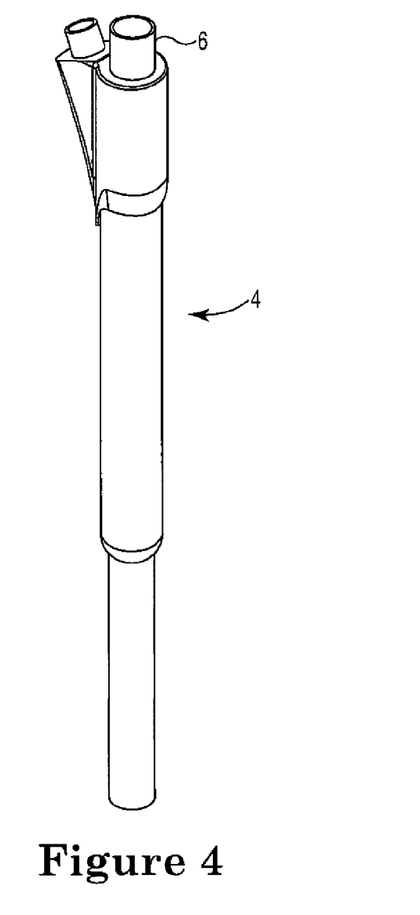
FIG. 4 is a perspective view of a centering rod that is positionable within a bone compactor of the invention.

FIG. 3 illustrates another embodiment a compactor 4 of the invention, which has a similar outer shape to that of the compactor 2. However, compactor 4 includes a hole or channel 5 extending through at least a portion of a length of its elongated member. With this embodiment, compactor 4 can be inflated and deflated via a pressure connector 3a, which is located adjacent to the elongated member of the compactor. Hole or channel 5 can be designed and constructed to accommodate the insertion of a centering rod therein, such as centering rod 6 illustrated in FIG. 4. A portion of a proximal end of the centering rod 6 can extend beyond the proximal end of the compactor 4, as illustrated. Centering rod 6 can be used to assist in the accurate centering and alignment of the compactor 4 inside the femur during its insertion.

Figure 5:
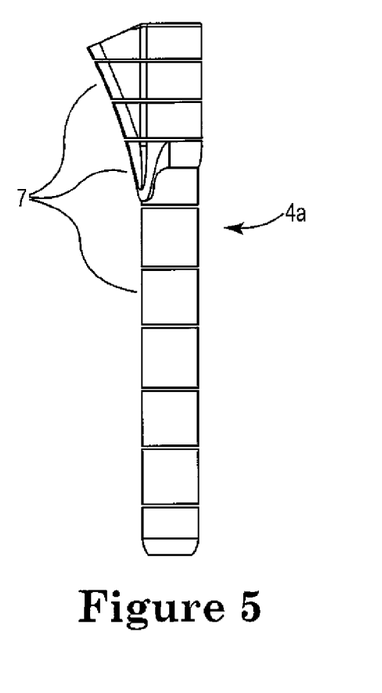
FIG. 5 is a front view of another embodiment of a bone compactor of the invention, which includes multiple expandable segments.

In yet another embodiment of the invention, a compactor 4a can be composed of multiple discrete segments 7 that are positioned adjacent to each other to make up a desired overall compactor size and shape, such as is illustrated in FIG. 5. Each of these segments 7 can be an inflatable or expandable balloon-type structure that can be used to compact the cancellous bone in a generally similar manner as other inflatable compactors described herein. Although ten of such segments 7 are illustrated relative to compactor 4 of FIG. 5, it is understood that more or less than ten segments can be used for this embodiment of a compactor of the invention. Each segment is an inflatable or expandable member (e.g., an expandable balloon) that is made of a relatively flexible material (such as rubber, plastic, impermeable fabric, or combination thereof, for example). The materials from which each segment is made can be the same or different from the materials from which the other segments of a particular compactor are made. For example, it may be desirable that some segment(s) are easier or harder to inflate than other segment(s) along a length of a compactor when each segment of that compactor is subjected to the same pressure.

In one embodiment of compactor 4a, each segment 7 is inflated or expanded individually in a pattern or sequence, such as from a distal to proximal direction, from a proximal to a distal direction, or in some other sequence of pattern. In an inflation sequence that involves sequential inflation of adjacent segments 7, a first segment at one end of the compactor 4a is inflated, and after this segment is inflated, an adjacent segment or more than one adjacent segment is inflated while the first segment can be deflated or partially deflated. By using this method of dividing the length of the compactor 4a into multiple segments 7 that are individually inflatable or expandable, the expansion force acting on the entire femur or other bone at any given time will be minimized. In other words, the sequential expansion of the segments 7 will concentrate the expansion forces to one area of the bone at a time, rather than exerting the force over the entire length of the compactor at once. Such a force distribution can be advantageous for certain patients and bone conditions, for example.

Figure 6:
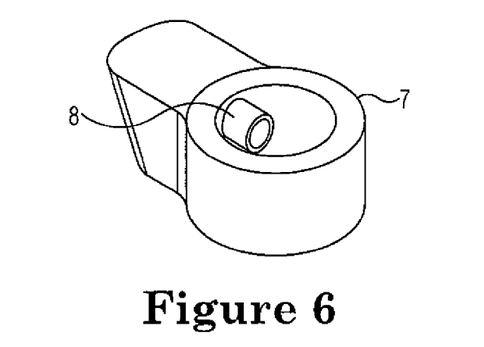
FIG. 6 is a perspective view of an expandable segment of a bone compactor of the invention, including a pressure connector.
Figure 7:
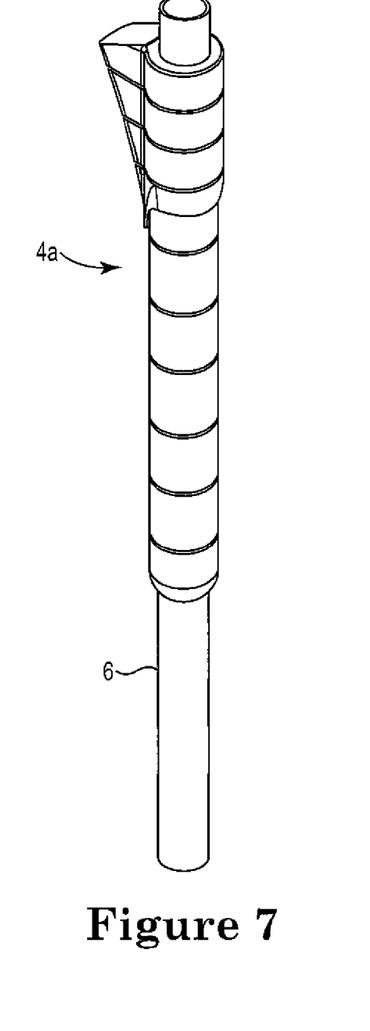
FIG. 7 is a perspective view of the bone compactor illustrated in FIG. 5, as positioned relative to a centering rod.

FIG. 6 shows an individual expandable segment 7 with a pressure connector 8 through which a gas or liquid inflating medium can be passed to inflate and deflate the segment. Each of the balloon segments 7 can be attached to a centering rod, such as centering rod 6 (illustrated in FIG. 7). As with other embodiments described herein, the multiple segments are sized, shaped, and arranged in such a way that the outer surface of the compactor 4a will take on the general shape of the hip stem prosthesis (e.g., hip stem prosthesis 1 described above) when all segments are inflated by a desired amount, as is shown in FIG. 7.

Figure 8A:
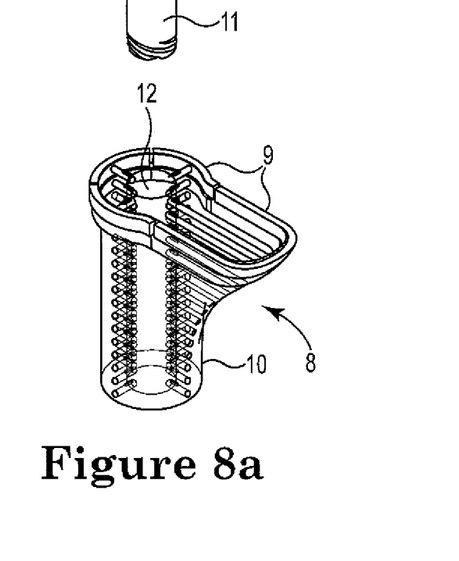
FIG. 8a is perspective view of another embodiment of a compactor of the invention, which is shown as partially transparent for better visibility of its internal components, along with a push rod positioned above a hole in the compactor.
Figure 8B:
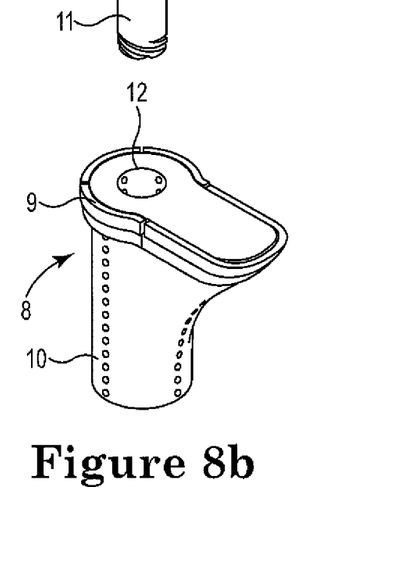
FIG. 8b is a perspective view of the compactor and push rod of FIG. 8a, with its components illustrated as generally opaque rather than transparent.
Figure 8C:
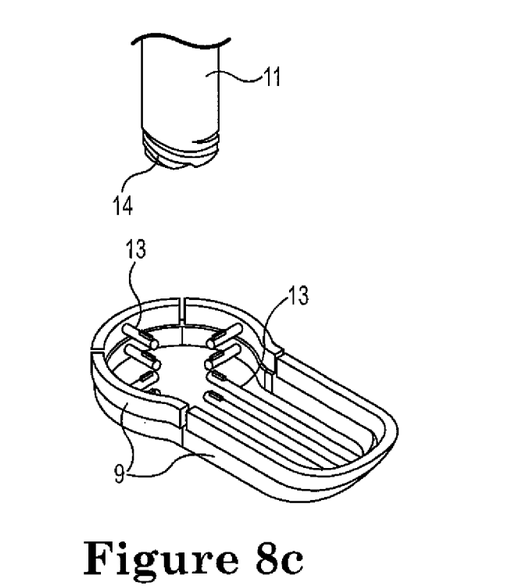
FIG. 8c is a perspective view of one expandable ring segment of the type that is used in the compactors of FIGS. 8a and 8b.

In another embodiment of the invention, segmental compression of cancellous bone is achieved using mechanical means. FIGS. 8a and 8b illustrate a mechanical compactor 8 composed of one or more expandable ring sections 9 assembled over a core member 10. FIG. 8c illustrates two of the exemplary ring sections 9 of FIGS. 8a and 8b, each of which is illustrated as having four subsections around its perimeter, wherein each subsection includes an outer frame that can conform to the final shape of the femoral cavity in which it will be positioned along with one or more pushpins 13. It is understood that the ring sections may alternatively include more or less than four subsections. It is further understood that each subsection can include more than one pushpin 13 or that one or more of the subsections do not have any pushpins 13. In an alternative embodiment, there is no structure provided over the pushpins 13, such that the ends of the pushpins themselves will be outwardly expandable relative to the bone, as described below.

FIG. 8a shows the compactor 8 as partially transparent for better visibility of its internal components and structure, while FIG. 8b illustrates the same compactor 8 without any of the components being shown as transparent. Each expandable ring section 9 can be expanded through mechanical means for example, by a push rod 11 being inserted into a hole 12 in core 10, as shown in FIGS. 8a and 8b. In particular, when the expandable ring section 9 is in its unexpanded state, the pushpins 13 are protruding at least slightly into the inner opening of hole 12. As a push rod 11 is pushed and/or twisted into the hole 12, the pushpin or pushpins 13 of each subsection of expandable ring section 9 can engage a series of spiral grooves 14 of push rod 11, which will thereby push each subsection of expandable ring section 9 outwardly relative to the hole 12. In one embodiment, the spiral grooves 14 of the push rod 11 are relatively deep at the distal end of the push rod 11, and gradually become more shallow when moving upward (i.e., in a proximal direction) until the depth essentially goes to zero (i.e., this portion of the push rod is relatively smooth), in order to be at the same level as the outside diameter of push rod 11. Alternatively, the push rod 11 can also be designed to have a reduced outside diameter slightly above the spiral grooves 14 so that there is no pushing force exerted on push pins 13 when the push pins 13 are adjacent to this reduced diameter portion. This configuration will cause one or more ring sections 9 to expand and retract one after another in sequence. In this way, the force acting on the femur will be minimized, as is discussed above. Other expandable ring configurations and means of expanding the rings are also contemplated and are considered to be within the scope of the present invention.

Figure 9:
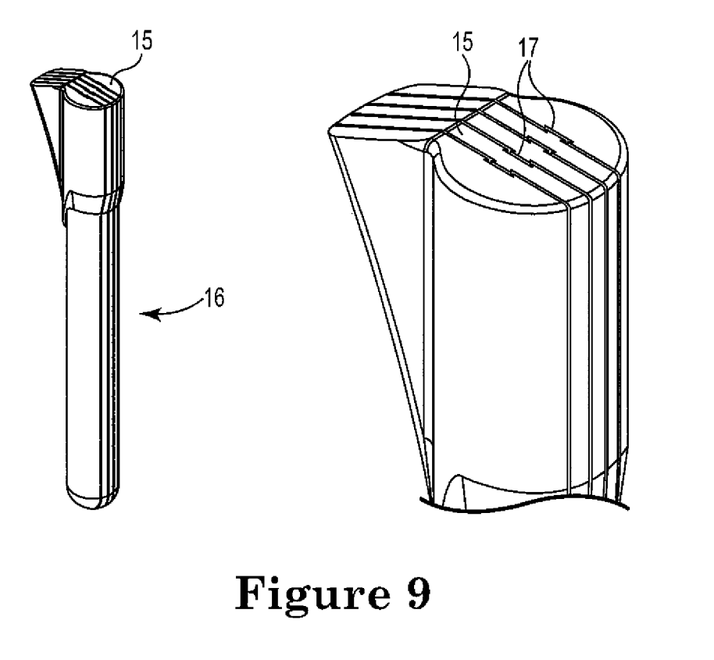
FIG. 9 includes a perspective view of another bone compactor of the invention, along with an enlarged view of an end portion of that bone compactor.

In another embodiment of the invention illustrated in FIG. 9, a bone compactor 16 is illustrated, which includes multiple longitudinal sections 15. With this bone compactor 16, bone compaction is achieved in a sequential manner by inserting the longitudinal sections 15 of sectional compactor 16 one at a time into the bone cavity. The longitudinal sections 15 can be coupled to each other through dovetail connections 17, for example, or can be coupled to each other in another manner. It is also contemplated that the sections 15 are not coupled to each other, although the coupling aspect of the sections helps to keep the longitudinal sections 15 properly oriented relative to each other, thereby maintaining the desired shape of the sectional compactor 16 when all the longitudinal sections 15 have been fully inserted into the bone. Inserting the each longitudinal section 15 into the bone sequentially can minimize the expansion force acting on the femur at any single time. Although the compactor 16 is shown as having five individual segments or sections 15, it is understood that the compactor 16 can instead include more or less than five of such segments or sections.

In accordance with any or all of the embodiments of the invention, it is contemplated that the bone in which the compactor is to be inserted is "pre-cracked" prior to insertion of that compactor in order to better prepare the bone for compaction. One advantage that can be provided by such a pre-cracking process is that the force required to compact the bone with a compactor can be reduced. The amount of advantage gained can depend on the compaction amount required, the bone size, and the bone quality. An embodiment of a tool that can be used for such a process can be a device comprising a plurality of teeth that can open up before implanting the compactor, such as an expanding tool 18 illustrated in the exemplary embodiment of FIG. 10. As shown, expanding tool 18 includes a lateral member 19 and a medial member 20, which can be pivoted relative to each other about a pivot point 21. Lateral member 19 can remain generally fixed or stationary, while medial member 20 can open or move in the direction of arrow 24. Alternatively, lateral member 19 can also open or move laterally.

Figure 10:
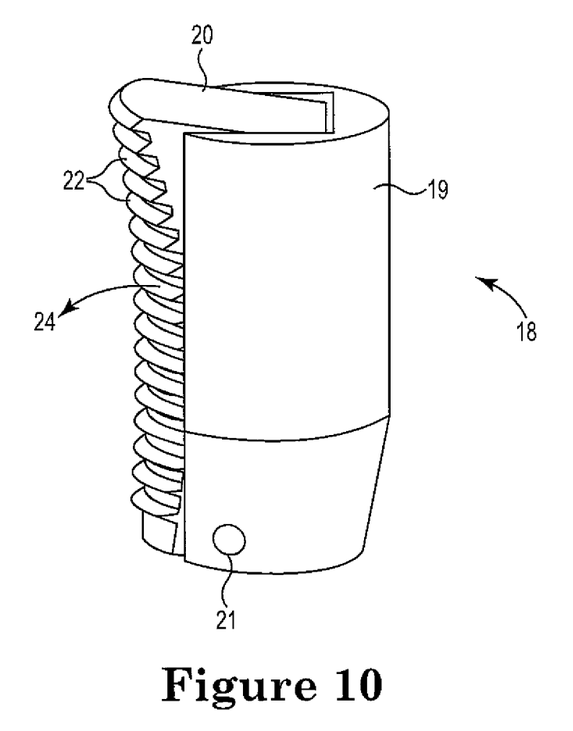
FIG. 10 is a perspective view of a tool used for pre-cracking a bone prior to insertion of a bone compactor.

Medial member 20 is shown with a plurality of teeth 22 spaced from each other along the height of tool 18. The illustrated teeth 22 of this Figure provide just one exemplary arrangement of teeth; however, it is understood that the tool may instead include more or less teeth that each have shapes and sizes that are similar or different from the illustrated teeth. Each of the teeth 22 can be relatively shallow and may be generally wedge or triangular shaped such that a point is inserted into the bone and pushed into the bone to increase the size of the bone crack or opening. The teeth of such a device can be symmetric or asymmetric, depending on the desired shape of the cracks that will be created. In addition, although teeth 22 are only shown on medial member 20, teeth can alternatively or additionally be provided on lateral member 19. AS a further alternative, expanding tool 18 can be configured without any teeth and can instead be used as a bone compactor by expanding or opening lateral member 19 and medial member 20 relative to each other about pivot 21.

Figure 11:
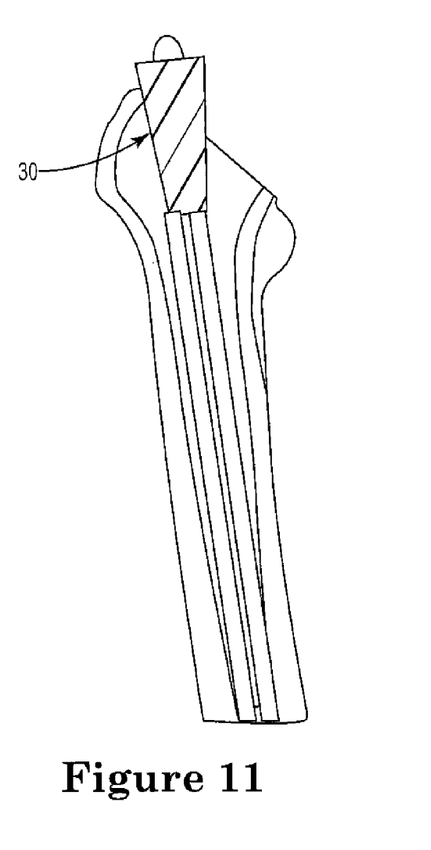
FIG. 11 is a front cross-sectional view of a reamer positioned within a proximal femur.
Figure 12:
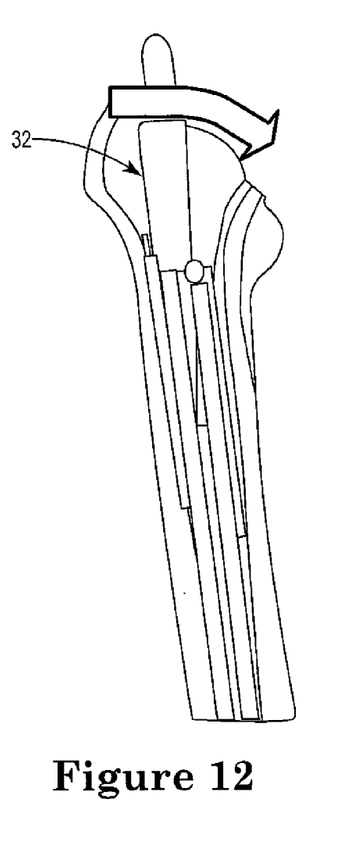
FIG. 12 is a front cross-sectional view of a tool of the type illustrated in FIG. 10 positioned within a femur, with the tool in an open configuration.

FIG. 11 is a front cross-sectional view of a reamer 30 positioned within a proximal femur, and FIG. 12 is a front cross-sectional view of a tool 32 of the type illustrated in FIG. 10 positioned within a femur, with the tool 32 in an open configuration. Insertion of the tool 32 and/or any compactors of the invention can be accomplished using vibratory force in certain cases where insertion via hammer blows would not be desirable. Further, compaction of the bone is directed primarily in a medial direction, due to the lateral location of a straight intramedullary alignment rod relative to the bone in which it is inserted. In one exemplary insertion method, a reamer is used to ream at least a portion of a proximal bone, and then a correspond size of alignment rod can be inserted. After the rod is inserted, a cannulated pre-cracking tool can then optionally be slid over the alignment rod, and can be gently tapped or pressed to initiate cracks in a desired compaction zone of the bone. A compactor, which may be hinged, can then be slid over the alignment rod, where the rod and compactor are positioned to ensure that the compaction will occur in a medial direction. Controlled compaction can then be achieved by actuating the compaction hinge, for example, and monitoring force feedback. If desired, the compaction hinge can be locked in its deployed condition, which can then be used as a trial prosthesis.

The present invention has now been described with reference to several embodiments thereof. The entire disclosure of any patent or patent application identified herein is hereby incorporated by reference. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the structures described herein, but only by the structures described and claimed herein and the equivalents of those structures.

The invention claimed is:

1. A bone compacting device for compacting cancellous bone within a bone cavity in combination with a push rod, the bone compacting device comprising:
   a body comprising a plurality of segments, wherein each segment comprises a ring portion, and wherein each segment is adjacent to at least one adjacent segment between a first end and a second end of the body and along a length of the body;
   a core member extending along the length of the body and through the ring portion of each of the plurality of segments, the core member comprising a central opening;
   wherein each of the plurality of segments comprises a plurality of sub-segments around its perimeter, and wherein at least one of the sub-segments comprises at least one inwardly projecting pushpin member that is slideable relative to a corresponding aperture in the core member so that the sub-segments are independently moveable relative to the core member to contact the cancellous bone; and
   the push rod being insertable into the central opening of the core member and comprising at least one spiral groove around its outer surface and along at least a portion of its length, wherein each groove is engageable with at least one of the pushpin members to push the corresponding sub-segment outwardly relative to the central opening of the core member.

2. The combination of claim 1, wherein each of the segments comprises the same expandable material as the other segments.

3. The combination of claim 1, wherein at least one of the plurality of segments comprises a different expandable material than at least one other of the plurality of segments.

4. The combination of claim 1, wherein the core member comprises an outer surface over which the plurality of segments are adjacently positioned.

5. The combination of claim 1, wherein each of the sub-segments is outwardly moveable relative to the core member.

6. The combination of claim 1, wherein each of the plurality of sub-segments comprises at least one pushpin member extending inwardly from an inner surface and toward the core member.

7. The combination of claim 1, wherein the push rod is slideable within the body of the bone compacting device along its length.

8. The combination of claim 1, wherein a depth of the at least one spiral groove is greatest at a distal end of the push rod and decreases toward a proximal end of the push rod.

9. The combination of claim 1, wherein the at least one spiral groove extends along a first portion of the push rod, and wherein a second portion of the push rod that is adjacent to the first portion comprises a smaller outer diameter than the first portion.

10. The combination of claim 1, further in combination with an expanding tool for pre-cracking a bone surrounding the bone cavity before inserting the bone compacting device in the bone cavity.

* * * * *